United States Patent
Govari

(10) Patent No.: US 10,307,072 B1
(45) Date of Patent: Jun. 4, 2019

(54) REDUCING NOISE LEVELS ASSOCIATED WITH SENSED ECG SIGNALS

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/813,359

(22) Filed: Nov. 15, 2017

(51) Int. Cl.
*A61B 5/0408* (2006.01)
*A61B 5/00* (2006.01)
*A61B 5/0402* (2006.01)
*A61B 5/0452* (2006.01)

(52) U.S. Cl.
CPC ........ *A61B 5/04085* (2013.01); *A61B 5/0006* (2013.01); *A61B 5/0402* (2013.01); *A61B 5/0452* (2013.01); *A61B 5/6801* (2013.01); *A61B 5/6805* (2013.01); *A61B 5/6823* (2013.01); *A61B 5/7203* (2013.01); *A61B 5/742* (2013.01)

(58) Field of Classification Search
CPC . A61B 5/04085; A61B 5/0402; A61B 5/6823; A61B 5/6805; A61B 5/0452; A61B 5/0006; A61B 5/6801; A61B 5/742; A61B 5/7203
See application file for complete search history.

(56) References Cited

U.S. PATENT DOCUMENTS

| 6,681,003 B2* | 1/2004 | Linder | A61B 5/0006 379/106.02 |
| 2011/0288605 A1* | 11/2011 | Kaib | A61B 5/0006 607/5 |
| 2014/0213879 A1 | 7/2014 | Choe et al. | |
| 2014/0323892 A1* | 10/2014 | Ghosh | A61B 5/044 600/510 |
| 2015/0087951 A1 | 3/2015 | Felix et al. | |
| 2015/0257647 A1 | 9/2015 | Buck et al. | |
| 2015/0351690 A1 | 12/2015 | Toth et al. | |
| 2016/0022161 A1* | 1/2016 | Khair | A61B 5/0408 600/345 |

* cited by examiner

*Primary Examiner* — John P. Dulka
(74) *Attorney, Agent, or Firm* — Vincent J. Serrao

(57) ABSTRACT

A medical device includes multiple electrodes and a processor. The multiple electrodes are coupled to a substrate attached externally to a patient and are configured to sense multiple respective electrical signals from an organ of the patient. The processor is configured to estimate two or more noise levels associated with the electrical signals sensed by two or more respective pairs of the electrodes, to select the electrical signals having a smallest noise level from among the two or more noise levels, and to provide only the selected electrical signals for analysis.

22 Claims, 2 Drawing Sheets

REDUCING NOISE LEVELS ASSOCIATED WITH SENSED ECG SIGNALS

FIELD OF THE INVENTION

The present invention relates generally to electrocardiogram (ECG) signals, and particularly to methods and systems for reducing noise levels associated with sensed ECG signals.

BACKGROUND OF THE INVENTION

In various medical procedures, patches may be attached to a patient's body for monitoring electrical signals from an organ of the patient.

For example, U.S. Patent Application Publication 2015/0351690 describes systems, devices, methods, and kits for monitoring one or more physiologic and/or physical signals from a subject. A system including patches and corresponding modules for wirelessly monitoring physiologic and/or physical signals, and an isolating patch for providing a barrier between a handheld monitoring device with a plurality of contact pads and a subject are disclosed.

U.S. Patent Application Publication 2015/0257647 describes an improved method, system and product to provide wireless ECG patient monitoring. Although embodiments make specific reference to monitoring electrocardiogram signal with an adherent patch, the system methods, and device herein may be applicable to any application in which physiological monitoring is used. The invention also presents a reliable means for docking the interface while minimizing signal interference and user error.

U.S. Patent Application Publication 2015/0087951 describes a wearable monitor that includes a flexible extended wear electrode patch and a removable reusable monitor recorder. A pair of flexile wires is interlaced or sewn into a flexible backing, serving as electrode signal pickup and electrode circuit traces. The wearable monitor sits centrally on the patient's chest along the sternum, which significantly improves the ability to sense cutaneous cardiac electric signals, particularly those generated by the atrium.

SUMMARY OF THE INVENTION

An embodiment of the present invention that is described herein provides a medical device including multiple electrodes and a processor. The multiple electrodes are coupled to a substrate attached externally to a patient and are configured to sense multiple respective electrical signals from an organ of the patient. The processor is configured to estimate two or more noise levels associated with the electrical signals sensed by two or more respective pairs of the electrodes, to select the electrical signals having a smallest noise level from among the two or more noise levels, and to provide only the selected electrical signals for analysis.

In some embodiments, the organ includes a heart of the patient, and the electrical signals include electrocardiogram (ECG) signals sensed from the heart. In other embodiments, the medical device includes a reference electrode, which is coupled to the substrate and is configured to sense reference electrical signals from the organ of the patient. In yet other embodiments, the multiple electrodes are arranged in a circular configuration about the reference electrode.

In an embodiment, the medical device includes a wireless communication module, which is configured to transmit the selected electrical signals to an external unit. In another embodiment, the medical device includes a memory coupled to the substrate, the processor is configured to store the selected electrical signals in the memory.

In some embodiments, the medical device includes a readout interface for communicating with an external unit, the processor is configured to send the selected electrical signals, via the readout interface, to the external unit. In other embodiments, the multiple electrodes include at least a first pair of electrodes lying on a first axis, and a second pair of electrodes lying on a second axis, different from the first axis.

There is additionally provided, in accordance with an embodiment of the present invention, a method including sensing multiple electrical signals from an organ of a patient, using multiple respective electrodes that are coupled to a substrate and are attached externally to the patient. Two or more noise levels associated with the electrical signals sensed by two or more respective pairs of the electrodes are estimated. The electrical signals having a smallest noise level from among the two or more noise levels are selected. Only the selected electrical signals are provided for analysis.

The present invention will be more fully understood from the following detailed description of the embodiments thereof, taken together with the drawings in which:

DETAILED DESCRIPTION OF EMBODIMENTS

Overview

Figure 1:
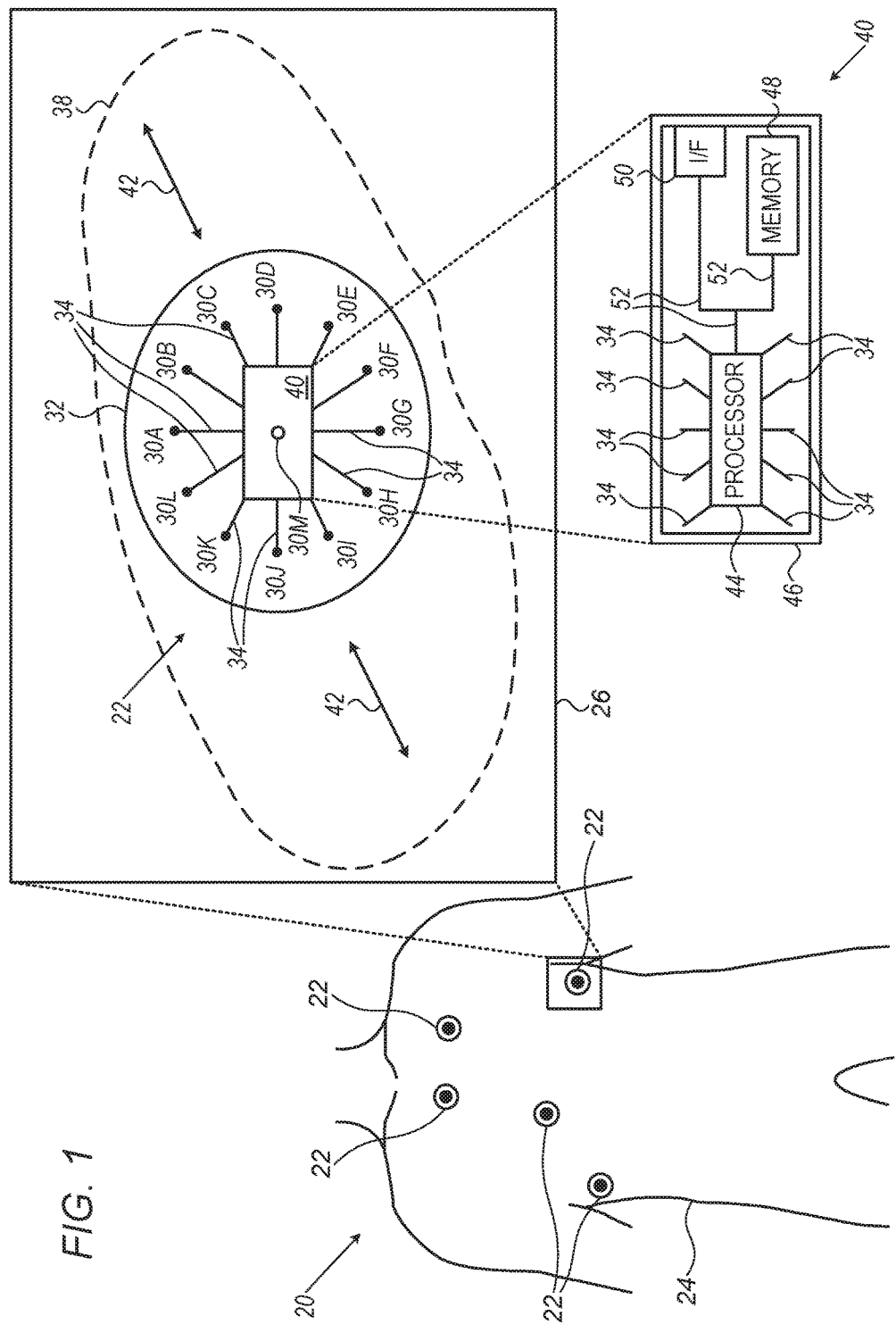
FIG. 1 is a schematic pictorial illustration of an electrocardiogram (ECG) monitoring system, in accordance with an embodiment of the present invention.

Cardiac irregularities, such as intermittent arrhythmias, are typically monitored using patches attached to the patient's body. Each of the patches typically comprises an electrode that senses electrocardiogram (ECG) signals from a patient heart. Typically, the sensed signals are distorted and may include noise caused by various sources, such as muscular activity. It is important to recover the clean ECG signals from the sensed noisy ECG signals, so as to enable effective monitoring of these cardiac irregularities.

Embodiments of the present invention that are described hereinbelow provide improved methods and systems for reducing noise levels associated with sensed ECG signals.

In some embodiments, a medical device, such as a patch attached externally to a patient body, comprises multiple electrodes configured to sense multiple respective ECG signals originating from the patient heart.

In some embodiments, the electrodes are connected to a processor, which is configured to designate various pairs of electrodes, and to estimate a respective noise level associated with the ECG signals sensed by each pair. In some embodiments, the processor is further configured to select the ECG signals having the smallest noise level from among the multiple estimated noise levels, and to store only the selected ECG signals in a memory. The processor may later export the stored ECG signals to an external unit.

In some embodiments, the electrodes are arranged in a circle about a reference electrode. This geometry is useful for mitigating noise caused by muscular activity or by any other source of noise having a directional character. In this configuration, ECG signals sensed by a pair of electrodes positioned in parallel to the muscle, typically differ from one another, thereby having high level of noise associated with the sensed ECG signals. In a circular geometry, at least one given pair of electrodes is substantially orthogonal to the direction of contraction and relaxation of the muscle. Therefore, the level of noise associated with the ECG signals sensed by the given pair is typically low.

In an embodiment, the processor refers to the ECG signals sensed by the reference electrode as a baseline signal, and calculates differences between the baseline signal and the respective ECG signals sensed by the other electrodes. In this embodiment, the processor is configured to select two ECG signals corresponding to two respective electrodes for which the calculated differences are the smallest.

In another embodiment, the reference electrode is not available, or not used for sensing a baseline signal. In this embodiment, the processor is configured to compare among the ECG signals acquired by all electrodes (excluding the reference electrode), and to select from among the electrodes, a pair of electrodes for which the difference between the respective ECG signals is minimal.

The disclosed techniques are effective in reducing the noise associated with the sensed ECG signals and configured to adapt to any change in the characteristics of the noise by selecting, in every measurement, the signals sensed by the best-performing pair of electrodes, from multiple pairs of electrodes having different orientations.

Furthermore, by discarding all but the best-performing ECG signals, the disclosed techniques enable long monitoring periods using a small volume of memory resources.

System Description

FIG. 1 is a schematic pictorial illustration of an electrocardiogram (ECG) monitoring system 20, in accordance with an embodiment of the present invention. In some embodiments, system 20 is configured to sense ECG signals from a heart (not shown) of a patient 24, so as to monitor cardiac irregularities, such as intermittent arrhythmias.

In some embodiments, system 20 comprises one or more external patches 22 adapted to adhere to the skin of patient 24. In the example of FIG. 1, system 20 comprises five patches 22, but may alternatively comprise any suitable number of patches 22 coupled to the skin of patient 24 in any suitable configuration.

In some embodiments, each patch 22 comprises multiple electrodes (shown in an inset 26) configured to sense ECG signals from the patient heart. In an embodiment, patch 22 is configured to send the sensed ECG signals to an external unit (not shown), either wirelessly or using a cable connection. In the example of FIG. 1, patch 22 further comprises a wireless module, which is configured to send the sensed ECG signals to an external receiver, using any suitable wireless technique.

In other embodiments that are not shown in FIG. 1, system 20 may comprise a portable monitoring device, such as an implanted device or a Holter monitor and wiring connecting between each patch 22 and the Holter monitor. In these embodiments, the sensed ECG signals are conducted, via the wires, from patches 22 to the Holter monitor, which is configured to store the ECG signals in a local memory of the Holter monitor and to transmit the stored ECG signals to the external receiver, e.g., on a daily bases.

Reducing Noise from the Sensed ECG Signals

Reference is now made to inset 26. In some embodiments, patch 22 comprises a substrate 32, which is configured to adhere to the skin of patient 24, and thereby, to attach a plurality of elements depicted herein to the skin of patient 24. In the example of FIG. 1, patch 22 is placed over a muscle 38 that contracts in a direction represented by arrows 42.

In some embodiments, patch 22 comprises a plurality of electrodes, e.g., twelve electrodes 30A . . . L, and a reference electrode 30M. In an embodiment, electrodes 30A . . . M are coupled to the body of patient 24 and are configured to sense electrical signals, such as the ECG signals, originating from the heart of patient 24.

In some embodiments, patch 22 further comprises a processing unit 40, which is electrically connected to electrodes 30A . . . M, via respective electrical wires 34. In some embodiments, electrodes 30A . . . L are arranged in a circle that is centered about reference electrode 30M, as shown in FIG. 1, or in any other suitable configuration.

Reference is now made to an inset 46. In some embodiments, processing unit 40 comprises a processor 44, which is configured to receive, via wires 34, the ECG signals from electrodes 30A . . . M. In an embodiments, processing unit 40 further comprises a memory 48, connected to processor 44 via wires 52. Processor 44 selects one or more ECG signals from among the ECG signals sensed using electrodes 30A . . . M, and stores these selected ECG signals in memory 48.

In some embodiments, processing unit 40 further comprises a readout interface 50, which is configured to receive ECG signals from processor 44, and to send these signals to an external unit (e.g., the external receiver described above). In some embodiments, interface 50 comprises a wireless communication module, which is configured to send these signals to the external unit, using any suitable wireless communication technique. In other embodiments, interface 50 comprises a connector module (not shown), which is configured to connect between processing unit 40 and the external unit, via a suitable communication cable.

In some embodiments, wires 34 are configured to withstand changes in respective distances between processing unit 40 and each electrode among electrodes 30A . . . L, which is typically caused by contraction and relaxation of muscle 38.

In other words, contraction and relaxation of muscle 38 may change the length of respective wires 34, without disconnecting processing unit 40 from any of electrodes 30A . . . L.

In some embodiments, processor 44 is configured to estimate two or more noise levels associated with the ECG signals sensed by two or more respective pairs of electrodes among electrodes 30A . . . L.

In an embodiment, processor 44 refers to the ECG signals sensed by reference electrode 30M as a baseline signal, and is configured to calculate differences between the baseline signal and the respective ECG signals sensed by electrodes 30A . . . L. In this embodiment, processor 44 is configured to select two ECG signals corresponding to two respective electrodes from among electrodes 30A . . . L, for which the calculated differences are the smallest.

In another embodiment, reference electrode 30M is not available, or not used for sensing the baseline signal. In this embodiment, processor 44 is configured to compare among the ECG signals acquired by electrodes 30A . . . L, and to select from among electrodes 30A . . . L, a pair of electrodes for which the difference between the respective ECG signals is minimal.

In alternative embodiments, processor 44 may apply any other suitable technique to select, from among electrodes 30A . . . L, the two electrodes having the smallest noise level.

For example, a pair of electrodes 30C and 30l are located substantially parallel to the stretching and relaxing directions of muscle 38, represented by arrows 42. In response to a contraction/relaxation of muscle 38 in direction 42, at least some of the electrodes move, thereby causing noise artifacts associated with the measured ECG signals. The noise level is typically proportional to the extent of motion.

In the present example, the motion is substantially in the direction of arrow 42. Therefore, the noise level associated with the ECG signals sensed by electrodes 30C and 30l is expected to be higher than the noise level of other pairs of electrodes among electrodes 30A . . . L. Note that the level of noise induced by the muscle movement that distorts the ECG signals sensed by a pair of electrodes, changes as a function of the angle between a line on which the electrodes lie and the muscle axis.

For example, electrodes 30L and 30F and reference electrode 30M lie on a line that is substantially orthogonal to the muscle axis represented by arrow 42. Therefore, any movement in the direction of arrow 42 (e.g., due to contraction and relaxation of muscle 38) may cause only a minimal movement of reference electrode 30M and of electrodes 30L and 30F. In response to a contraction of muscle 38, the noise level associated with the ECG signals sensed by electrodes 30L and 30F is expected to be lower than the noise level of any other pair of electrodes among electrodes 30A . . . L.

Note that for any pair of electrodes selected from among electrodes 30A . . . L, any movement of the electrodes relative to the heart, or movement of the electrodes relative to reference electrode 30M and relative to one another, may increase the noise level associated with the ECG signals sensed by these electrodes.

As described above, processor 44 is configured to estimate two or more noise levels associated with the ECG signals sensed by two or more respective pairs of electrodes among electrodes 30A . . . L. Subsequently, processor 44 is configured to select the electrical signals that have the smallest noise level, to store only these best-performing electrical signals in memory 48, and to discard all other electrical signals having noise level larger than the selected signals.

In some embodiments, the ECG monitoring described above may be carried out continuously for a predefined period of time (e.g., a week). In an embodiment, in the course of the week, processor 44 is configured to send the electrical signals stored in memory 48, via interface 50, to the external unit.

The configuration of patch 22 shown in FIG. 1 is an example configuration, which is chosen purely for the sake of conceptual clarity. In alternative embodiments, any other suitable configuration can also be used. The different elements of patch 22 may be implemented using any suitable hardware, such as in an Application-Specific Integrated Circuit (ASIC) or Field-Programmable Gate Array (FPGA). In some embodiments, some or all of the functions of processor 44 can be implemented using software, or using a combination of hardware and software elements. Memory 48 may comprise any suitable volatile or non-volatile memory, e.g., Random Access Memory (RAM) or Flash memory. Patch 22 typically also comprises a suitable battery or other power source (not shown).

Processor 44 typically comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The embodiments described herein focus mainly on sensing and transmission of ECG signals. The configuration of system 20 is provided by way of example, for demonstrating an example system or device in which ECG signals are acquired, analyzed to extract the ECG signals comprising the least associated noise, and sent to a suitable external unit. This configuration, however, is chosen purely for the sake of conceptual clarity. In alternative embodiments, the disclosed techniques can be used, mutatis mutandis, in various other configurations of electrodes, sensors and communication schemes. For example, the electrodes may be arranged in any geometric configuration in which one pair of electrodes lies on a first axis, and another pair of electrodes lies in a second, different axis.

In some embodiments, a given electrode among electrodes 30A . . . L may participate in more than one pair of electrodes. For example, three electrodes located in three respective vertices of a triangle. This configuration provides three pairs of electrodes along three respective axes (i.e., edges of the triangle).

Figure 2:
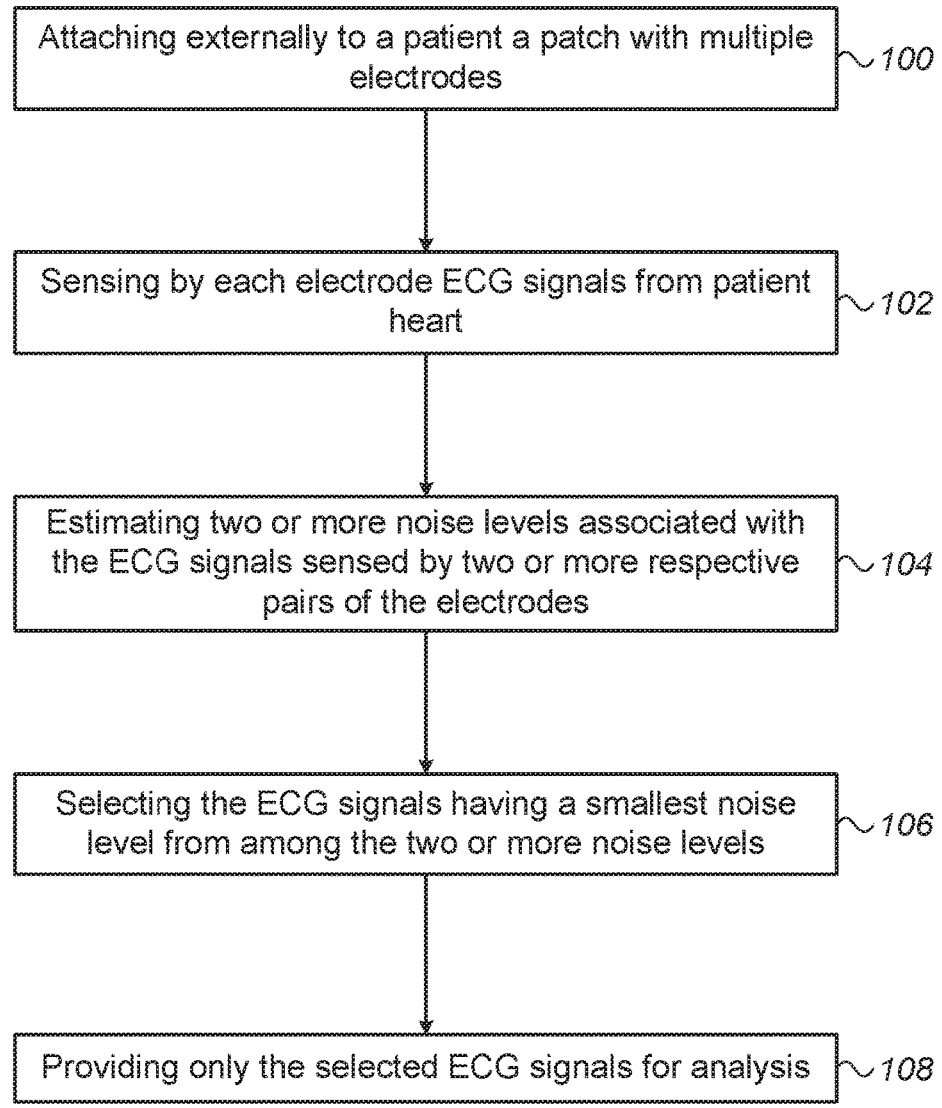
FIG. 2 is a flow chart that schematically illustrates a method for monitoring ECG signals, in accordance with an embodiment of the present invention.

FIG. 2 is a flow chart that schematically illustrates a method for monitoring ECG signals, in accordance with an embodiment of the present invention. The method begins with attaching, by an operator, such as a physician or a nurse, one or more patches 22 externally to the body of patient 24, at a patch placement step 100.

In some embodiments, each patch 22 comprises multiple electrodes, such as electrodes 30A . . . L, and reference electrode 30M. In some embodiments, electrodes 30A . . . M are configured to sense electrical signals, such as ECG signals, from an organ (e.g., heart) of patient 24.

In some embodiments, patch 22 further comprises processor 44 of processing unit 40, which is configured to receive the sensed ECG signals from electrodes 30A . . . M.

At a signal acquisition step 102, processor 44, receives from electrodes 30A . . . M the sensed ECG signals acquired from the heart of patient 24.

At a noise estimation step 104, processor 44 estimates two or more noise levels associated with the ECG signals sensed by two or more respective pairs of electrodes among electrodes 30A . . . L. In some embodiments, processor 44 refers to the ECG signals sensed by reference electrode 30M as a baseline signal, and calculates differences between the baseline signal and the respective ECG signals sensed by electrodes 30A . . . L. In this embodiment, processor 44 selects two ECG signals corresponding to two respective electrodes from among electrodes 30A . . . L, for which the calculated differences are the smallest.

In another embodiment, reference electrode 30M is not used for sensing the baseline signal. In this embodiment, processor 44 compares among the ECG signals acquired by electrodes 30A . . . L, and selects from among electrodes 30A . . . L, a pair of electrodes for which the difference between the respective ECG signals is minimal.

At a signal selection step 106, processor 44 selects, based on the estimation carried out at step 104, the ECG signals having the smallest noise level from among the noise levels of the ECG signals received from the respective pairs of electrodes. In some embodiments, processor 44 selects the signals received from the pair of electrodes 30L and 30F. In the example of FIG. 1, the noise level received from the ECG signals of electrodes 30L and 30F have the smallest noise level from among any other pair of electrodes from among electrodes 30A . . . L.

At a signal provision step 108, processor 44 stores in memory 48 the ECG signals that were selected at step 106, and typically discards the other ECG signals having noise level larger that the selected signals.

Note that the noise mechanisms may change in time and may differ between patches 22. For example, in FIG. 1 muscle 38, which is located near the left ribs of patient 24, was assumed the main source of noise associated with the ECG signals acquired by electrodes 30A . . . M, e.g., due to stretching and relaxing during respiration. In other embodiments, the noise mechanism at any other patch 22 may be related to another muscular activity having a different orientation, or to any other source of noise. For example, movement of chest muscles of patient 24.

In some embodiments, processor 44 repeats steps 102-108, such that a new selected ECG signal is stored in memory 48 once every 1-2 seconds. In some embodiments, processor sends the signals stored in memory 48, e.g., via interface 50, to the external unit on a daily basis. Processor 44 may delete the sent signals from memory 48 or alternatively archives them for further analysis. In an embodiment, the external unit is configured to analyze the signals for monitoring cardiac irregularities, such as intermittent arrhythmias, in the heart of patient 24.

In other embodiments, processor 44 is further configured to analyze the signals stored in memory 48, so as to provide the patient with a warning indication in response to detecting substantial irregularities in at least part of the analyzed signals.

Although the embodiments described herein mainly address ECG signals, the methods and systems described herein can also be used in other applications, such as in electroencephalogram (EEG).

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical device, comprising:
a patch having multiple electrodes coupled to a substrate attached externally to a patient, the multiple electrodes being configured to sense multiple respective electrical signals from an organ of the patient, the multiple electrodes including a plurality of pairs of electrodes, each pair of electrodes lying on an axis of the patch in the plane of the substrate different from the axis of every other pair of electrodes; and
a processor, which is configured to:
estimate noise levels associated with the electrical signals sensed by the plurality of pairs of electrodes;
select a pair of electrodes of the plurality of pairs of electrodes having two electrical signals with a smallest noise level from among the estimated noise levels; and
provide only the two electrical signals from the selected pair of electrodes for analysis.

2. The medical device according to claim 1, wherein the organ comprises a heart of the patient, and wherein the electrical signals comprise electrocardiogram (ECG) signals sensed from the heart.

3. The medical device according to claim 1, and comprising a reference electrode, which is coupled to the substrate and is configured to sense reference electrical signals from the organ of the patient.

4. The medical device according to claim 3, wherein the multiple electrodes are arranged in a circular configuration about the reference electrode.

5. The medical device according to claim 4, wherein the multiple electrodes are arranged in a circular configuration surrounding the reference electrode, wherein at least one of the plurality of pairs of electrodes is substantially orthogonal to a direction of contraction and relaxation of a muscle of the patient.

6. The medical device according to claim 3, wherein the processor is configured to estimate the noise levels by referring to the reference electrical signals from the organ of the patient as a baseline signal and calculating differences between the baseline signal and the electrical signals from the plurality of pairs of electrodes, and to select the pair of electrodes by selecting the two signals from the plurality of pairs of electrodes for which the calculated differences are the smallest.

7. The medical device according to claim 1, and comprising a wireless communication module, which is configured to transmit the selected electrical signals to an external unit.

8. The medical device according to claim 1, and comprising a memory coupled to the substrate, wherein the processor is configured to store the selected electrical signals in the memory.

9. The medical device according to claim 1, and comprising a readout interface for communicating with an external unit, wherein the processor is configured to send the selected electrical signals, via the readout interface, to the external unit.

10. The medical device according to claim 1, wherein the processor is configured to estimate the noise levels by comparing the difference between the electrical signals of each of the plurality of pairs of electrodes and to select the pair of electrodes for which the difference between the electrical signals is the smallest.

11. The medical device according to claim 1, wherein the selected pair of electrodes are lying on an axis on the patch in the plane of the substrate substantially orthogonal to a direction of contraction and relaxation of a muscle of the patient.

12. A method, comprising:
sensing multiple electrical signals from an organ of a patient, using a patch having multiple respective electrodes coupled to a substrate and are attached externally to the patient;
estimating noise levels associated with the electrical signals sensed by a plurality of pairs of the electrodes, each pair of electrodes lying on an axis of the patch in the plane of the substrate different from the axis of every other pair of electrodes;

selecting a pair of electrodes of the plurality of pairs of electrodes having two electrical signals with a smallest noise level from among the estimated noise levels; and providing only the two electrical signals from the selected pair of electrodes for analysis.

13. The method according to claim 12, wherein the organ comprises a heart of the patient, and wherein the electrical signals comprise electrocardiogram (ECG) signals sensed from the heart.

14. The method according to claim 12, and comprising sensing reference electrical signals from the organ of the patient, using a reference electrode.

15. The method according to claim 14, wherein the multiple electrodes are arranged in a circular configuration about the reference electrode.

16. The method according to claim 15, wherein the multiple electrodes are arranged in a circular configuration surrounding the reference electrode, wherein at least one of the plurality of pairs of electrodes is substantially orthogonal to a direction of contraction and relaxation of a muscle of the patient.

17. The method according to claim 14, wherein the processor is configured to estimate the noise levels by referring to the reference electrical signals from the organ of the patient as a baseline signal and calculating differences between the baseline signal and the electrical signals from the plurality of pairs of electrodes, and to select the pair of electrodes by selecting the two signals from the plurality of pairs of electrodes for which the calculated differences are the smallest.

18. The method according to claim 12, wherein the providing the selected electrical signals comprises transmitting the selected electrical signals wirelessly for the analysis.

19. The method according to claim 12, wherein the providing the selected electrical signals comprises storing the selected electrical signals in a memory coupled to the substrate.

20. The method according to claim 12, wherein the providing the selected electrical signals comprises sending the selected electrical signals, via a readout interface coupled to the substrate, to an external unit.

21. The method according to claim 12, wherein the processor is configured to estimate the noise levels by comparing the difference between the electrical signals of each of the plurality of pairs of electrodes and to select the pair of electrodes for which the difference between the electrical signals is the smallest.

22. The method according to claim 12, wherein the selected pair of electrodes are lying on an axis on the patch in the plane of the substrate substantially orthogonal to a direction of contraction and relaxation of a muscle of the patient.

* * * * *